(12) United States Patent
Steffen

(10) Patent No.: US 10,035,003 B2
(45) Date of Patent: Jul. 31, 2018

(54) DUAL BALLOON DUAL SYRINGE DELIVERY DEVICE AND METHOD OF USE

(71) Applicant: Dennis L Steffen, Tavernier, FL (US)

(72) Inventor: Dennis L Steffen, Tavernier, FL (US)

(*) Notice: Subject to any disclaimer, the term of this patent is extended or adjusted under 35 U.S.C. 154(b) by 67 days.

(21) Appl. No.: 15/267,052

(22) Filed: Sep. 15, 2016

(65) Prior Publication Data

US 2017/0050002 A1     Feb. 23, 2017

Related U.S. Application Data

(63) Continuation-in-part of application No. 14/042,574, filed on Sep. 30, 2013, now Pat. No. 9,586,005, and a continuation-in-part of application No. 14/171,722, filed on Feb. 3, 2014, now Pat. No. 9,681,860.

(60) Provisional application No. 62/219,610, filed on Sep. 16, 2015.

(51) Int. Cl.
*A61M 25/10* (2013.01)
*A61M 5/19* (2006.01)
*A61B 17/12* (2006.01)

(52) U.S. Cl.
CPC ....... *A61M 25/10* (2013.01); *A61B 17/12109* (2013.01); *A61M 5/19* (2013.01); *A61M 25/1011* (2013.01); *A61B 17/12186* (2013.01); *A61B 2017/1205* (2013.01); *A61M 2025/105* (2013.01); *A61M 2025/1013* (2013.01)

(58) Field of Classification Search
CPC ...... A61M 25/10182; A61M 2025/105; A61M 2025/1013; A61M 5/19
USPC .................................................. 604/82, 191
See application file for complete search history.

(56) References Cited

U.S. PATENT DOCUMENTS

| | | | |
|---|---|---|---|
| 4,919,651 | A | 4/1990 | Doane |
| 7,645,261 | B2 | 1/2010 | Hinchliffe |
| 7,988,696 | B2 | 8/2011 | Lu et al. |
| 2006/0271092 | A1 | 11/2006 | Reed et al. |
| 2008/0171978 | A1 | 7/2008 | Quigley |
| 2011/0166547 | A1 | 7/2011 | Baumbach et al. |
| 2015/0005743 | A1 | 1/2015 | McCullough |

*Primary Examiner* — Nathan R Price
*Assistant Examiner* — Anh Bui

(57) ABSTRACT

The present invention relates to a dual balloon catheter with controlled expansion and solution flow, a multi-port manifold and a dual syringe delivery device and method with intended use in sclerotherapy.

14 Claims, 17 Drawing Sheets

SECTION 1-1

SECTION 2-2

SECTION 3-3

SECTION 4-4

SECTION 5-5

SECTION 5-5

DUAL BALLOON DUAL SYRINGE DELIVERY DEVICE AND METHOD OF USE

CROSS REFERENCES TO RELATED APPLICATIONS

This application claims the benefit under 35 U.S.C. § 119(e) of U.S. Provisional Application No. 62/219,610 filed on Sep. 16, 2015, and U.S. Non-Provisional application Ser. No. 14/042,574 filed on Sep. 30, 2013, and U.S. Non-Provisional application Ser. No. 14/171,722 filed on Feb. 3, 2014; the complete disclosure of which is incorporated herein by reference in its entirety.

FIELD OF THE INVENTION

The present invention relates to a dual balloon catheter with controlled expansion and solution flow, a multi-port manifold and a dual syringe delivery device and method of use. Although the invention may be adapted to uses other then described within this application the following description of the invention pertains to usage with sclerosing solutions and method (sclerotherapy) for the application of the sclerosing solution in the human vascular system. Sclerotherapy is a procedure used to treat blood vessels or blood vessel malformations (vascular malformations) and also those of the lymphatic system. A sclerosing solution is injected into the vessels, which makes them shrink. It is used for children and young adults with vascular or lymphatic malformations. When used in adults sclerotherapy is often used to treat spider veins, smaller varicose veins, and hemorrhoids.

Sclerotherapy is one method, along with surgery, radiofrequency and laser ablation for treatment of spider veins, occasionally varicose veins, and venous malformations. In ultrasound-guided sclerotherapy, ultrasound is used to visualize the underlying vein so the physician can deliver and monitor the injection site. Sclerotherapy often takes place under ultrasound guidance after venous abnormalities have been diagnosed with duplex ultrasound. Sclerotherapy under ultrasound guidance and using microfoam sclerosants has been shown to be effective in controlling reflux from the sapheno-femoral and sapheno-popliteal junctions. However, some medical professionals believe that sclerotherapy is not suitable for veins with reflux from the greater or lesser saphenous junction, or for veins with axial reflux.

INTRODUCTION

Conventional methods associated with Sclerotherapy and delivery of the sclerosing solution simply dispenses the solution into the targeted vein with limited precession which can result in a less desirable result. Injecting the abnormal veins with a sclerosing solution causes the target vein to immediately shrink, and which dissolve over a period of weeks as the body naturally absorbs the treated vein. Sclerotherapy is a non-invasive procedure normally taking just minutes to perform. The downtime is minimal, in comparison to an invasive varicose vein surgery.

Sclerotherapy is the preferred procedure and is preferred over laser for eliminating large spider veins (telangiectasiae) and smiler varicose leg veins. Compared to a laser, the sclerosing solution additionally closes the smaller feeder veins under the skin that are causing the spider veins to form, thereby making a recurrence of the spider veins in the treated area less likely. Multiple injections of dilute sclerosants are injected into the abnormal surface veins of the involved leg. It is common practice for the patient to require at least two treatment sessions separated by several weeks to significantly improve the appearance of the problem veins.

Sclerotherapy can also be performed using microfoam sclerosants under ultrasound guidance to treat larger varicose veins, including the great and small saphenous veins. In this procedure the physician maps the patient's varicose veins using ultrasound, as the veins are injected with the solution the procedure is monitored using ultrasound. Through ultrasound the sclerosing solution can be observed entering the vein, and if required further injections can be administered to allow all the abnormal veins to be treated. Follow-up ultrasound scans are used to confirm closure of the treated veins, and any residual abnormal veins can be identified and further treated.

A more preferred technique is Foam Sclerotherapy which is a technique that involves injecting a foamed sclerosing solution within a blood vessel using a pair of syringes, one syringe with sclerosing solution in it and one with gas (originally air) this is known as the Tessari method. The Tessari method was modified by the Whiteley-Patel modification which uses 3 syringes. The sclerosing solution (sodium tetradecyl sulfate or polidocanol) are mixed with air or a physiological gas (carbon dioxide) in a syringe or by using mechanical pumps thus foaming and increasing the surface area of the solution. The foam sclerosing solution is viewed as more efficacious than the non-foamed sclerosing solution in causing sclerosis (thickening of the vessel wall and sealing off the blood flow), foaming the sclerosing solution prevents it from mixing with the blood in the vessel instead the foamed solution displaces the blood, thus avoiding dilution of the solution and causing maximal sclerosing results. The foaming technique has also proven more effective for longer and larger veins. In some instances using foam sclerotherapy the foamed solution created has the consistency of tooth paste like foam for injections.

Although complications are rare, they can include venous thromboembolism, visual disturbances, allergic reaction, thrombophlebitis, skin necrosis, and hyperpigmentation or an inflamed treatment area.

If the sclerosing solution is injected properly into the vein, there is no damage to the surrounding skin, but if it is injected and penetrates the vein wall, the surrounding tissue may see necrosis and possible scarring can result. Skin necrosis is rare but can be cosmetically objectionable, and may take a sizable time period to heal. It is very rare when small amounts of dilute (<0.25%) sodium tetradecyl sulfate (STS) is used, but has been seen when higher concentrations (3%) are used. Blanching of the skin often occurs when STS is injected into arterioles (small artery branches) such as in telangiectatic matting.

The more common complications occur due to an intense inflammatory reaction to the sclerotherapy solution in the area surrounding the injection site of the vein Additionally systemic complications can potentially occur when the sclerosing solution traverses from the injection site in the veins to the heart, lung, or even the brain. Some recent incidents have attributed a stroke to foam treatment when an unusually large amount of foam was administered. Further incidents have shown that bubbles from even a small amount of sclerosing foam injected into the veins appeared in the heart, lung and brain. In summary studies have shown that foam sclerotherapy is safe when the proper procedural precautions and techniques are employed.

BRIEF DESCRIPTION

The present invention relates to a dual balloon, dual syringe delivery device consisting of multiple components which when collectively assembled result in a device with capability of accommodating syringe volume sizes from 1 ml through 5 ml and varying balloon volumes. As previously described there exist varying techniques for the application of sclerosing solution with syringes. The dual balloon catheter with manifold and solution channel insert employs a perforated outer balloon and inner expansion balloon joined to a catheter and joined to a manifold possessing dual syringe ports, and a guidewire port lying on the longitudinal centerline of the manifold, the dual balloon catheter with manifold is joined with two syringes one with a sclerosing solution and one with saline solution, the joined components are then loaded into the dual syringe delivery device and ready to use. The two syringes are deployed simultaneously, the sclerosing solution is deployed into the vein wall region through the outer perforated balloon while the saline solution fills/expanses the inner balloon in turn displacing the blood in the vein while forcing the sclerosing solution through the perforation orifices and into the vein wall In one embodiment, the invention utilizes a dual balloon catheter and manifold with solution channel insert paired with a dual syringe delivery device. The component construction may be accomplished by a range of medically compliant materials, e.g. TPU, polycarbonate, thermoplastic elastomer, ABS etc.

BRIEF DESCRIPTION OF THE DRAWINGS

The invention may be better understood and appreciated by reference to the detailed description of specific embodiments presented herein in conjunction with the accompanying drawings of which.

DETAILED DESCRIPTION

Figure 1:
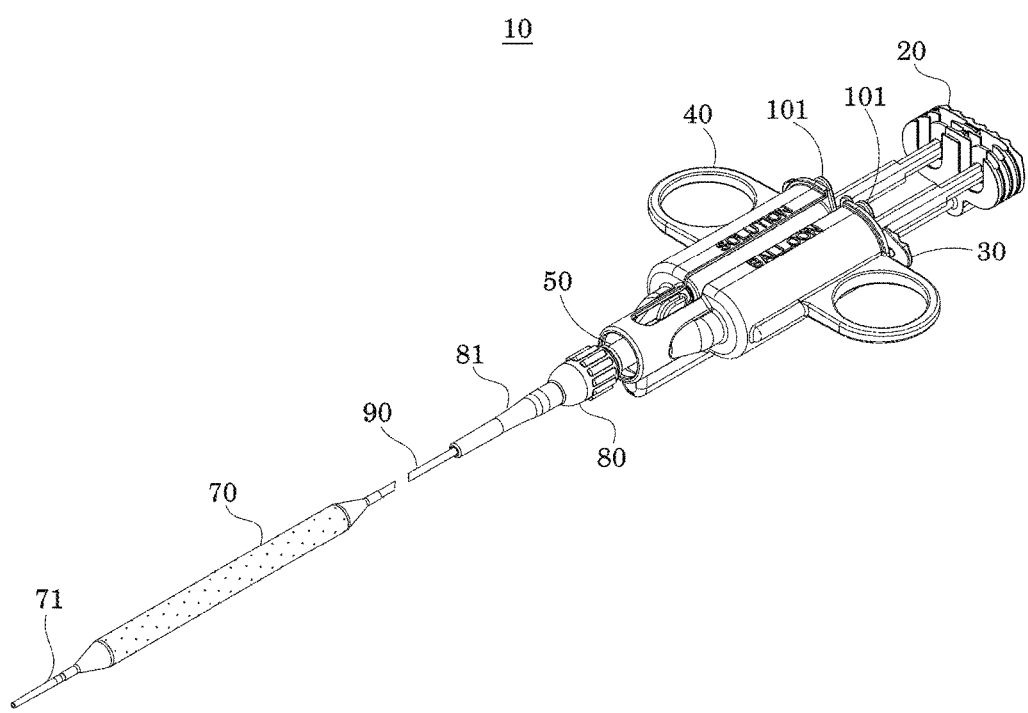
FIG. 1 is an isometric view of the primary components in the dual balloon dual syringe delivery device; the configuration illustrates the application with dual syringes and dual balloon catheter assembly, all in accordance with the invention.

A Dual Balloon Dual Syringe Delivery Device with controlled balloon inflation and solution deployment for the application of sclerosing solution embodying the principles of the invention is provided. The device comprises a dual balloon catheter assembly, cradle, plunger, and holster.

Before any embodiments of the invention are explained in detail, it is to be understood that the invention is not limited in its application to the details of the structure and function set forth in the following description or illustrated in the appended drawings. The invention is capable of other embodiments and of being practiced or of being carried out in various vays. Also, it is to be understood that the phraseology and terminology used herein is for the purpose of description and should not be regarded as limiting. The use of "including," "comprising." or "having" and variations thereof herein is meant to encompass the items listed thereafter and equivalents thereof as well as additional items. "Comprising" also encompasses the terms "consisting of" and "consisting essentially of." The use of "consisting essentially of" means, e.g., that a method may include additional steps, but only if the additional steps do not materially alter the basic and novel characteristics of the claimed method. Unless specified or limited otherwise, the terms "joined", "mounted," "connected," "supported," and "coupled" and variations thereof herein are used broadly and encompass both direct and indirect mountings, connections, supports, and couplings. Further. "connected" and "coupled" are not restricted to physical or mechanical connections or couplings.

No admission is made that any reference, including any patent or patent document, cited in this specification constitutes prior art. In particular, it will be understood that unless otherwise stated, reference to any document herein does not constitute an admission that any of these documents forms part of the common general knowledge in the art in the United States or in any other country. Any discussion of the references states what the author asserts and the applicant reserves the right to challenge the accuracy and pertinence of any of the documents cited herein.

As used in this specification and the appended claims, the singular forms "a," and "the" include plural referents unless the content clearly dictates otherwise. As used in this specification and the appended claims, the term "or" is generally employed in its sense including "and/or" unless the content clearly dictates otherwise.

Unless otherwise noted, technical terms are used according to conventional usage. However, as used herein, the following definitions may be useful in aiding the skilled practitioner in understanding the invention. Such definitions shall be applied, unless a different definition is given in the claims or elsewhere in this specification.

In view of the foregoing disadvantages inherent in conventional multi syringe sclerosing application systems/methods, the invention provides a novel device and method for application of a sclerosing solution. The invention provides a unique and cost effective method for the delivery of sclerosing solutions with capabilities to accommodate, varying solution volumes, varying balloon volumes, rate of flow, and rate of balloon expansion.

The full advantage of the Dual Balloon Dual Syringe Delivery Device pertains to its ability to easily handle a range of syringe sizes, balloon volumes, rate of flow, and balloon expansion control with one configuration; additionally the ease of use and simplicity of the design makes it a superior option over current delivery systems/methods. It should also be noted that during the surgical act of applying the sclerosing solution to the desired area, dilution and controlled deployment of the sclerosing solution as well as time is always an issue and this invention directly addresses these issues. In accordance with the invention, a surgeon is able to accurately deploy the sclerosing solution and avoid undue wasted time as in other systems/methods while attempting to assemble/load or match the syringe size to the system/method.

Figure 2:
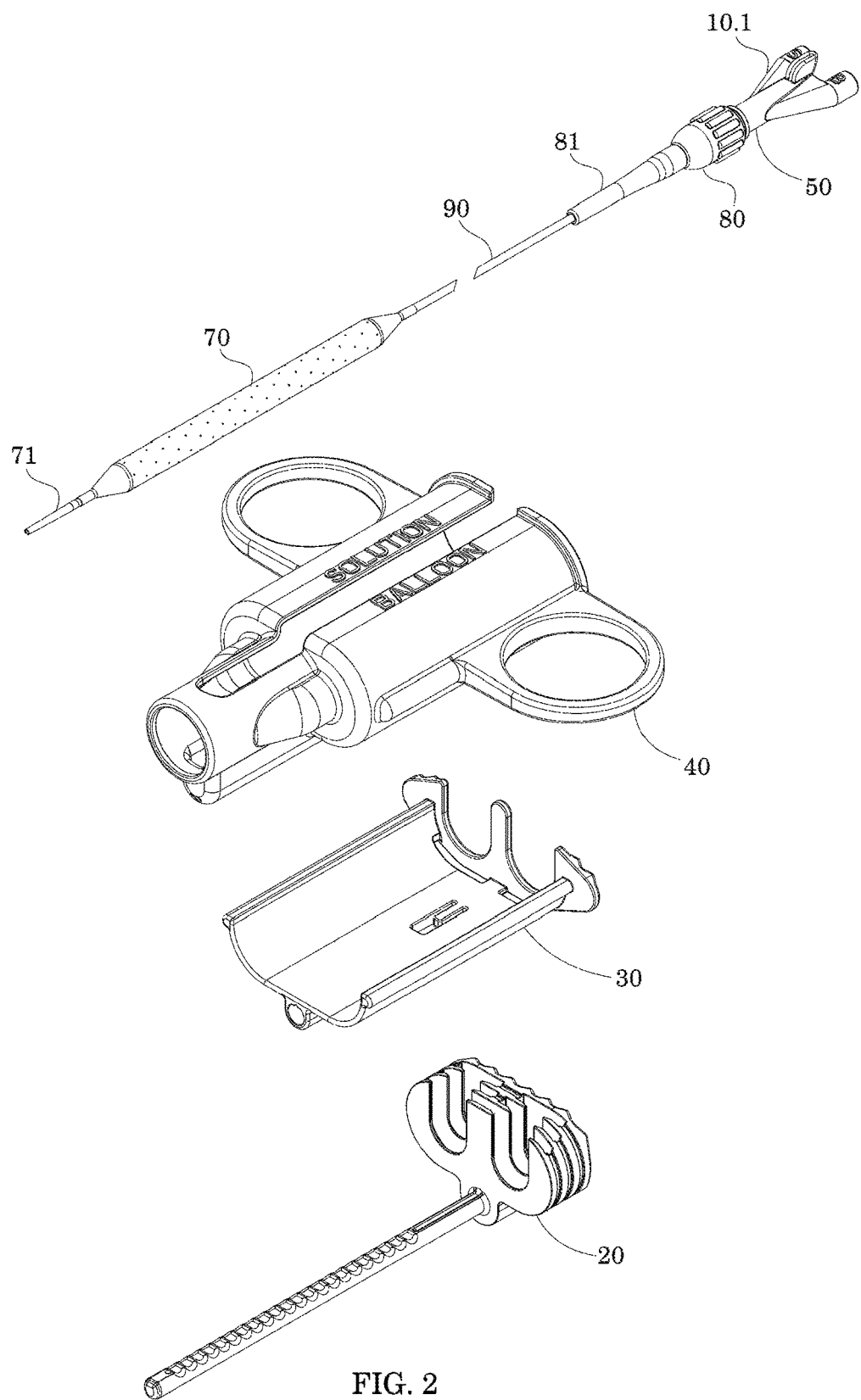
FIG. 2 is an isometric view of each of the four primary components, plunger, cradle, holster, and dual balloon catheter assembly of the dual balloon dual syringe delivery device, all in accordance with the invention.

Reference is now made to FIGS. 1-17 in which a Dual Balloon Dual Syringe Delivery Device, generally designated by reference numeral 10, in accordance with the invention is shown. Device 10 collectively comprised of a manifold 50, a solution channel insert 60, a multi-lumen 90, a distal lumen tip 71 (separate component or formed from end of lumen), a retainer cap 80, a proximal strain-relief 81, a distally positioned outer balloon 70 and inner balloon 75, a plunger 20, a cradle 30, and a holster 40 for delivery of sclerosing solutions. In an illustrated embodiment, FIG. 1 the final configuration of the plunger 20, cradle 30, holster 40, dual 2 ml syringes 101, and manifold 50, multi-lumen 90, distal lumen tip 71, retainer cap 80, proximal strain-relief 81, and distally positioned outer balloon 70 is defined. Additionally illustrated in FIG. 2 are the principle components, a dual balloon catheter 10.1 comprised of the manifold 50, solution channel insert 60, multi-lumen 90, distal lumen tip 71, retainer cap 80, proximal strain-relief 81, and distally positioned outer balloon 70 (and inner balloon 75 not illustrated), along with the plunger 20, cradle 30, and holster 40 which make up the device 10.

Figure 3:
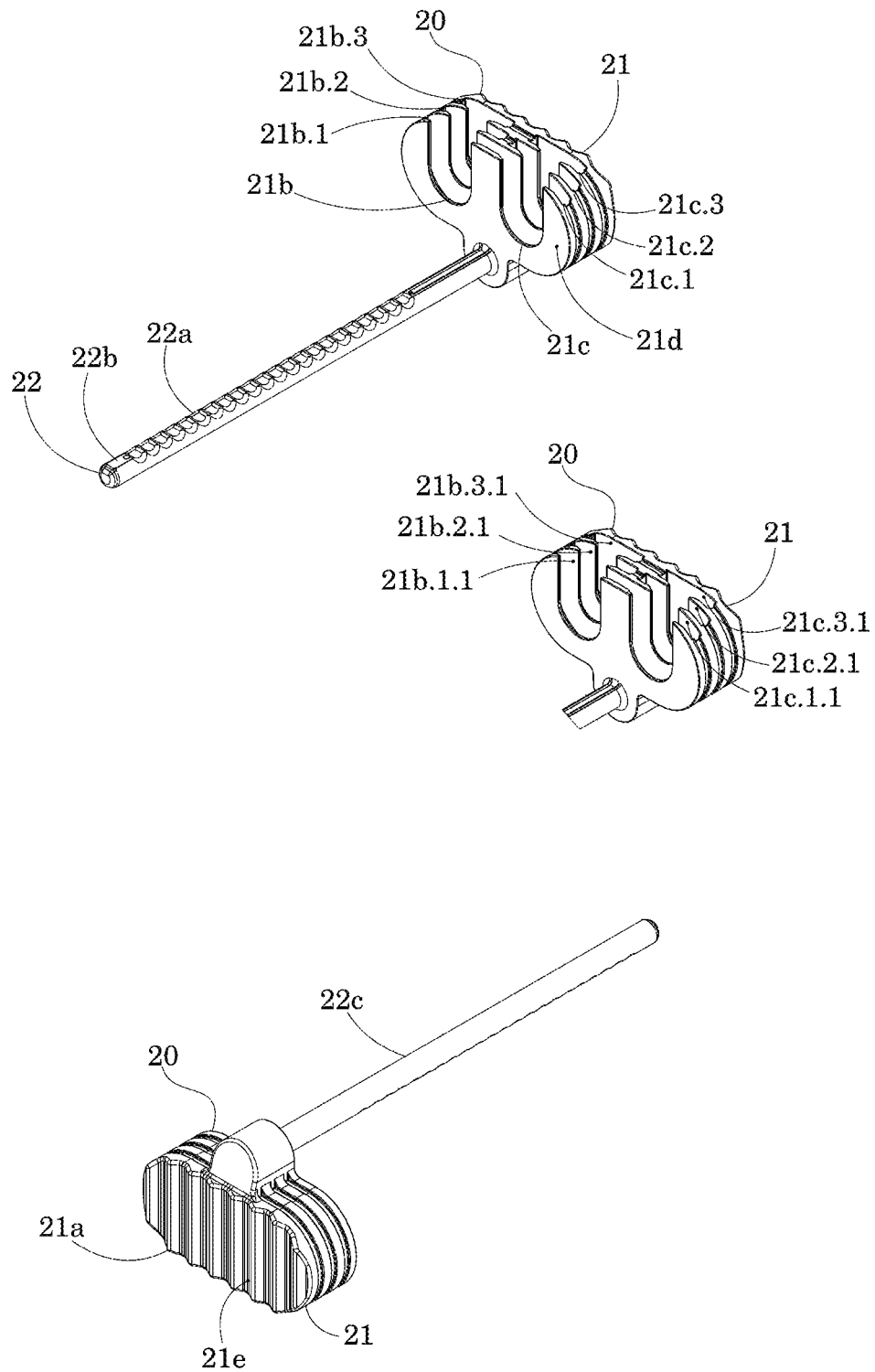
FIG. 3 is an isometric view of the plunger component of the dual balloon dual syringe delivery device, all in accordance with the invention.

As shown in FIG. 3, the plunger 20 is comprised of a head 21 obround in shape having a distal surface 21d and a proximal surface 21e, and having a shaft 22 cylindrical in shape and joined to the head at the distal surface 21d. The head 21 has a set of U shaped slots 21b and 21c extending from the distal surface 21d to surfaces 21b.3.1 and 21c.3.1 and being proportioned to allow passage of the syringe 101 plunger shaft 101a, additionally there are three sets of horizontal slots either side of the longitudinal centerline which are spaced and proportioned to accommodate the varying syringe plunge head 101b sizes and syringe plunger 101a stroke, one side 21b.1, 21b.2, 21b.3, and opposite 21c.1, 210.2, 21c.3 proportioned to allow passage of the syringe 101 plunger shaft head 101b, e.g. slots 21b.2 and 21c.2 which are proportion for a 2 ml syringe plunger head and positioned to allow the full stroke of the 2 ml syringe plunger stroke. In addition each horizontal slot has an upper surface 21b.1.1, 21b.2.1, 21b.3.1 and 21c.1.1, 21c.2.1, 21c.3.1 which contacts the top surface the syringe plunger shaft head 101b. The plunger 20 head 21 has a series of protrusion 21a on the proximal surface 21e to provide grip when the plunger is depressed during usage. The shaft 22 which is joined to the head 21 has a concave surface 22b to prevent rotation when inserted into aperture 33b and joined with the convex surface 33c of the cradle 30, and which faces in the direction of the slots 21b and 21c and extending from the most distal tip of the shaft 22 to surface 21d of the head 21, also a series of grooves 22a lying perpendicular to the longitudinal centerline and which face in the direction of the slots 21b and 21c on the head 21 the opposite surface of the shaft 22c is smooth and convex. The grooves 22a which come into contact with the detent tab 34 and pawl 34a located on the cradle 30 when the shaft 22 is inserted into the aperture 33b on the cradle 30. The grooves 22a and detent tab 34 and pawl 34a join to create a static positioning element to hold the plunger 20 in position relative to the cradle 30 to facilitate loading the syringe and dual balloon catheter 10.1.

Figure 4:
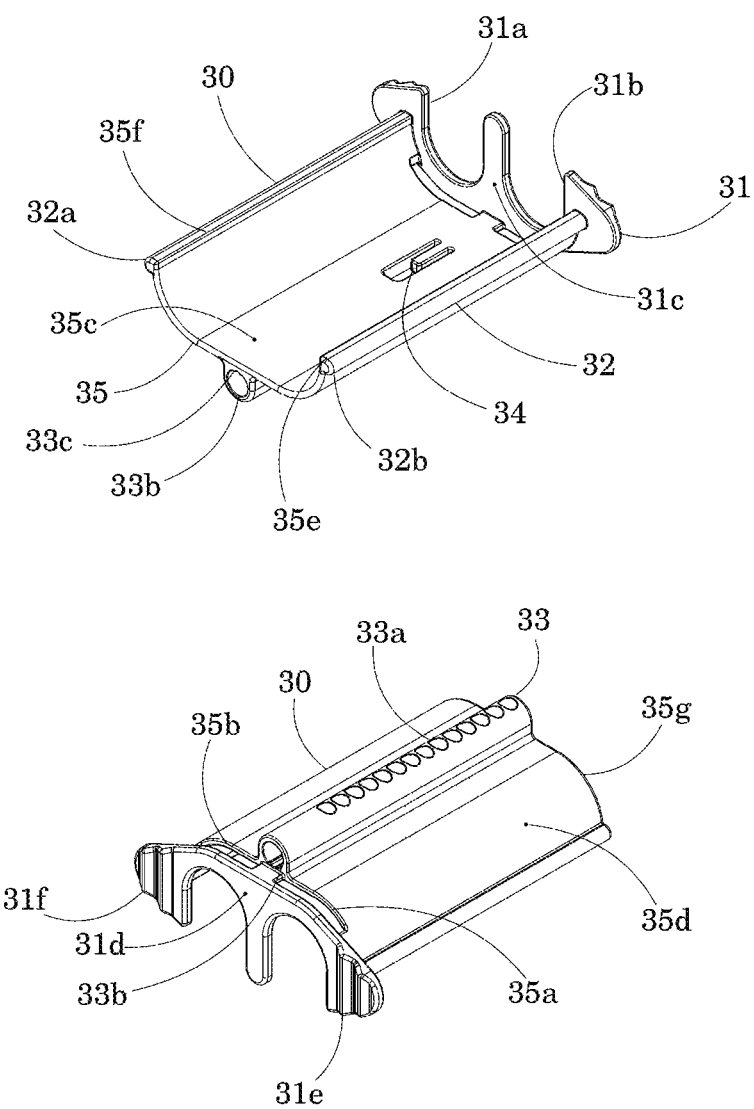
FIG. 4 is an isometric view of the cradle component of the dual balloon dual syringe delivery device, all in accordance with the invention.

As shown in FIG. 4, the cradle 30 comprised of a proximal flange 31 having a distal surface 31c and a proximal surface 31d which extends equally about the longitudinal centerline and is joined to a semi-obround body portion 35 having an interior surface 35c and an exterior surface 35d which extends distally with the outer edges extending equally about the longitudinal centerline and terminating at the longitudinal center plane. The proximal flange 31 has two U shaped slots 31a and 31b located either side of the longitudinal centerline extending from the distal surface 31c to the proximal surface 31d and proportioned to allow passage of the syringe 101 plunger shaft 101a, correspondently the body 35 has two apertures 35a and 35b extending from the interior surface 35c to the exterior surface 35d and positioned against the flange distal surface 31c and adjacent to the U shaped slots 31a and 31b located on the flange 31 and being proportioned to allow passage of the syringe 101 finger tab 101c. The flange 31 has raised elements 31e and 31f on the proximal surface 31d located at its outer extent about the longitudinal centerline. The body 35 has a tubular protrusion 33 located on the and joined to the exterior surface 35d and centered on the longitudinal centerline and extends from the most distal edge 35g of the body to the proximal end terminating parallel to the distal edges of the two apertures 35a and 35b, the tubular protrusion 33 has an aperture 33b which extends the length of the protrusion and which is proportioned to allow insertion of the shaft 22 of the plunger 20. In addition the tubular protrusion 33 has a series of grooves 33a lying perpendicular to the longitudinal centerline and facing in the direction opposite the body 35. The grooves 33a come into contact with the detent tab 42 and pawl 42a located on the holster 40 when the cradle 20 is inserted into the holster 40. The grooves 33a and detent tab 42 and pawl 42a join to create a static positioning element to hold the cradle 30 in position relative to the holster 40 once the; cradle 30, plunger 20, and dual balloon catheter configuration 10.b are assembled and inserted in the holster 40. A rail set 32 having a first rail 32a located on the outer extent of the body 35f and having a second rail 32b located on the outer extent of the body 35e which extend from the most distal edge 35g of the body 35 to the base of the distal surface 31c of the flange 31 and are proportioned to slide within the channels 46a and 46b located on the body 46 of the holster 40 when the two components are joined.

Figure 5:
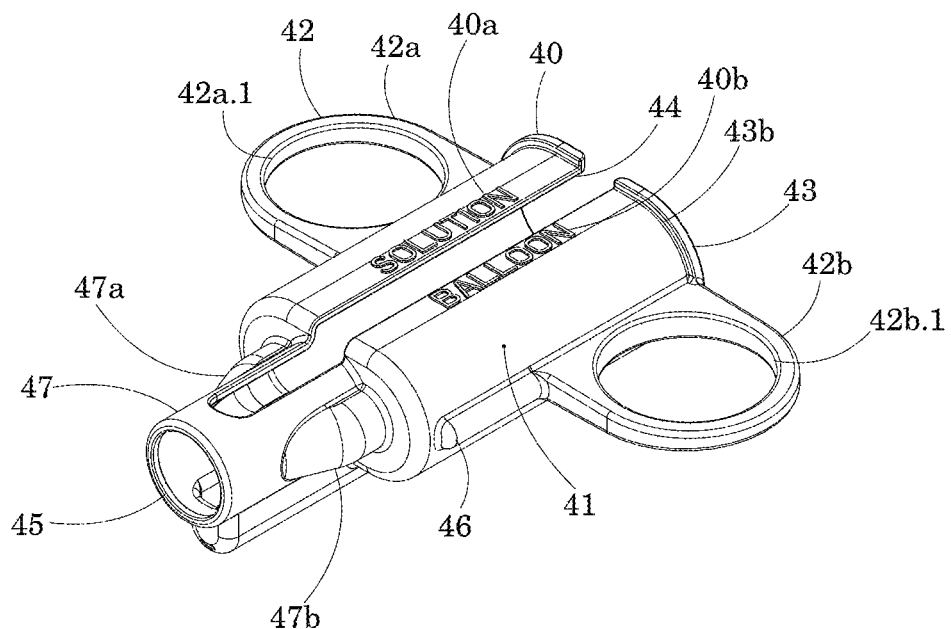
FIG. 5 is an isometric view of the holster component of the dual balloon dual syringe delivery device, all in accordance with the invention.
Figure 5:
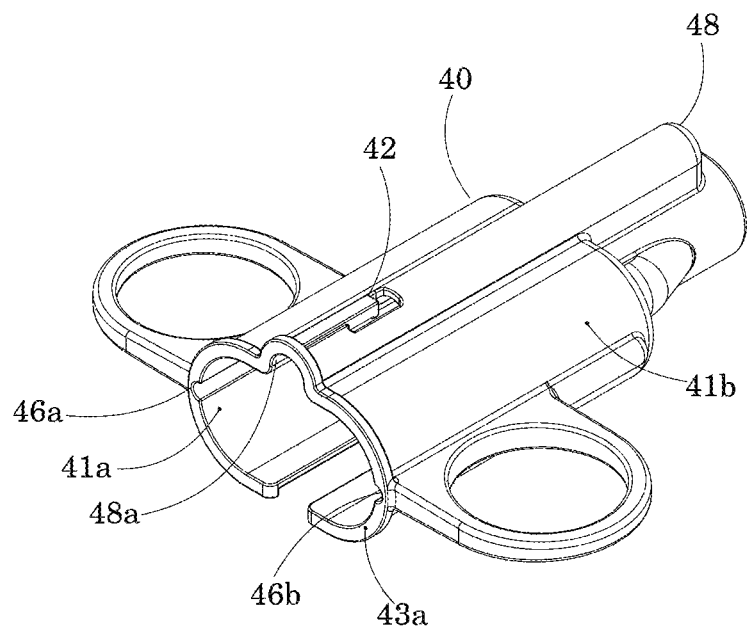

As shown in FIG. 5, the holster 40 comprised of a proximal flange 43 having a distal surface 43b and a proximal surface 43a which extends the perimeter of the body 41 and is flush to the interior surface of the body 41a and overhangs the exterior surface 41b of the body 41 the flange provides added rigidity to the body walls, the body 41 that extends distally has an interior surface 41a and an exterior surface 41b, and distal nose area 47. A dual finger loop 42 having a first loop 42a and a second loop 42b located on and joined to the exterior surface 41b of the body 41 extending distally and laterally equally about the longitudinal centerline and the longitudinal center plane and is proximally joined to the flange 43. The proximal flange 43 is interrupted equally either side of the longitudinal centerline by an aperture 44 which extends distally and which is proportioned to allow passage of the manifold 50 guidewire channel 50a. The dual finger loops 42a and 42b have apertures 42a.1 and 42b.1 proportioned to allow passage of an average sized human hand index finger and middle finger for gripping the device during usage. The distal nose area of the body 47 has an aperture 45 in the most distal tip which is proportioned to allow passage of the dual balloon catheter assembly 10.1 additionally in the distal nose area 47 are two contours 47a and 47b which mirror the contours 50b and 50c of the manifold 50, the contours 47a and 47b act as a physical stop against the manifold 50 when the device is fully assembled with the dual catheter assembly 10.1 along with the syringes 101, cradle 30 and plunger 20 as illustrated in 10.b then seated in the holster 4. Located on the inner surface 41a of the body 41 and opposite the aperture 44 is a U shaped channel 48 centered on the longitudinal centerline which extends from the most proximal surface 43a on the flange 43 distally to the distal nose area 47 located along this channel is a retention tab 42 with pawl 42a which joins with the grooves 33a on the cradle 30 as previously described. Alone the inner surface 41a of the body 41 a set of U shaped channels 46a and 46b centered on the longitudinal center plane and which extend from the most proximal surface 43a on the flange 43 distally along the length of the body 41. The U shaped channels are proportioned to allow passage of the rail set 32 located on the outer extent of the cradle body 35 as previously described when the two components are joined. The external surface of the body 41 is marked to further aid in orientation of the fluid solution reservoirs 40a for SOLUTION and 40b for BALLOON.

Figure 6:
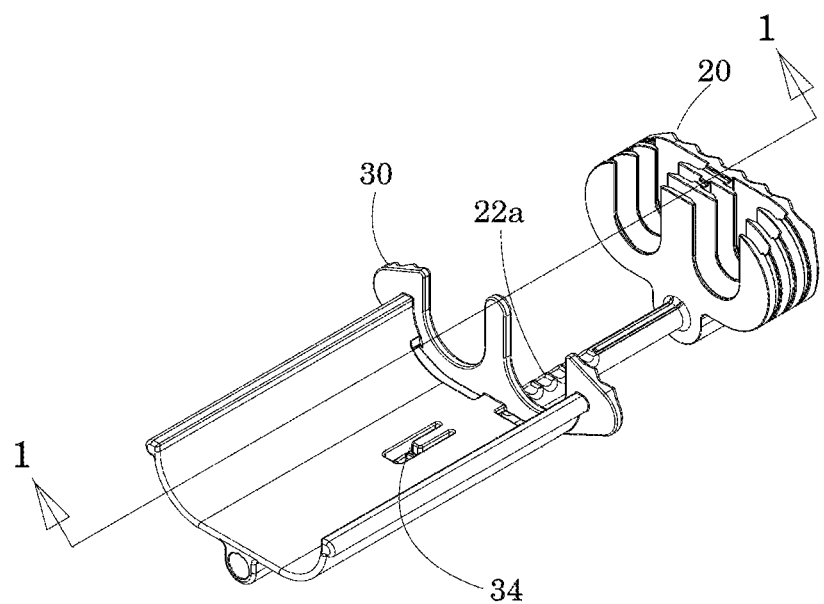
FIG. 6 is an isometric view and a longitudinal cross section of the plunger and cradle components as they would be configured in normal usage of the dual balloon dual syringe delivery device, all in accordance with the invention.
Figure 6:
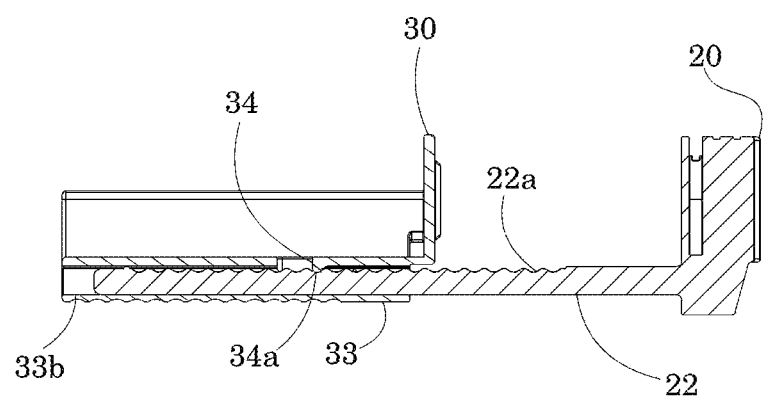

As shown in FIG. 6, the longitudinal centerline cross section 1-1 of the plunger 20 and cradle 30 as they would be joined together in normal use serve to further illustrate the relationship between component elements. The cross section further helps clarify the relationship of the retaining tab 34 and pawl 34a of the cradle 30 to the grooves 22a of the shaft 22 on the plunger 20; additionally it illustrates the shaft 22 of the plunger 20 as it is positioned in the aperture 33b of the cradle 30.

Figure 7:
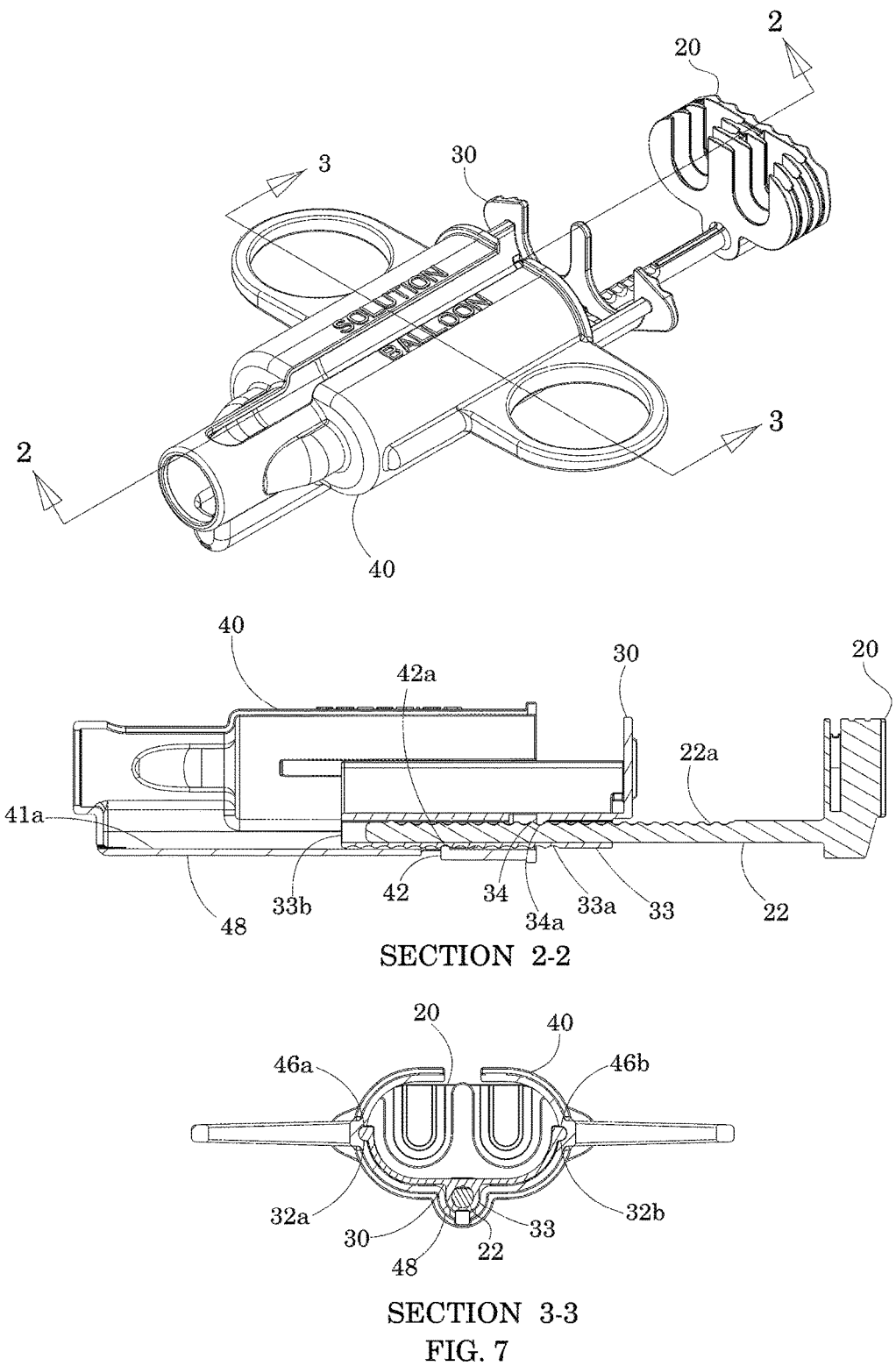
FIG. 7 is an isometric view, longitudinal and lateral cross sections, of the plunger, cradle and holster components as they would be configured in normal usage of the dual balloon dual syringe delivery device, all in accordance with the invention.

As shown in FIG. 7, the longitudinal centerline cross section and the lateral cross section 3-3 of the plunger 20, cradle 30 and holster 40 as they would be joined together in normal use serve to further illustrate the relationship between component elements. The longitudinal cross section 2-2 further clarifies the relationship of the retaining tab 42 and pawl 42a of the holster 40 to the grooves 33a of the cradle 30. The lateral cross section 3-3 further clarifies the relationship of the side rails 32a and 32b of the cradle 30 and how they interface with the channels 46a and 46b of the holster 40; additionally it illustrates the interface between the U shaped protrusion 33 of the cradle 30 as it is positioned in the U shaped channel 48 of the holster 40.

Figure 8:
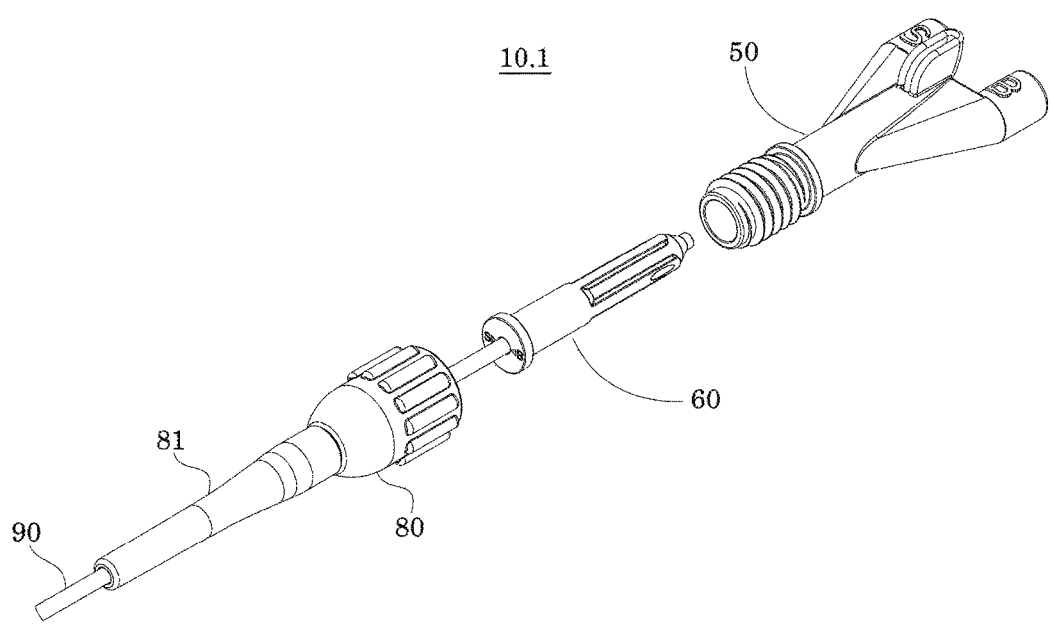
FIG. 8 is an exploded isometric partial view of the normal progression/method of joining the dual balloon catheter with the manifold into the completed final catheter assembly as it would be configured in normal usage of the dual balloon dual syringe delivery device, all in accordance with the invention.

As shown in FIG. 8, illustrates the method of assembly of the multi-lumen 90, solution channel insert 60, manifold 50, retainer cap 80 strain-relief 81, (distal lumen tip 71, inner balloon 75, and outer balloon 70, not illustrated) to comprise the dual balloon catheter assembly 10.1.

As shown in FIGS. 9, 10, 11, and 12 in which an illustrated embodiment, manifold 50 is defined by non-converging unvalved first solution channel 51b and an unvalved second solution channel 51c which are opposed to the isolated unvalved guidewire channel 51a. Manifold 50 connects to two solution sources (e.g. syringes each syringe containing a fluid solution) via the two luer connector fittings 51c.2, and 51b.2 which are configured to ISO 594-1 and -2 standard for 6% taper luer fittings. As presented in this specification the configuration of one unvalved guidewire channel 51a and two female slip luer fittings of the unvalved solution channels 51b and 51c of the manifold 50 can optionally be configured in varying combinations depending on requirements or as all female slip luer fittings or all female locking luer fittings (not illustrated in specification).

Figure 11:
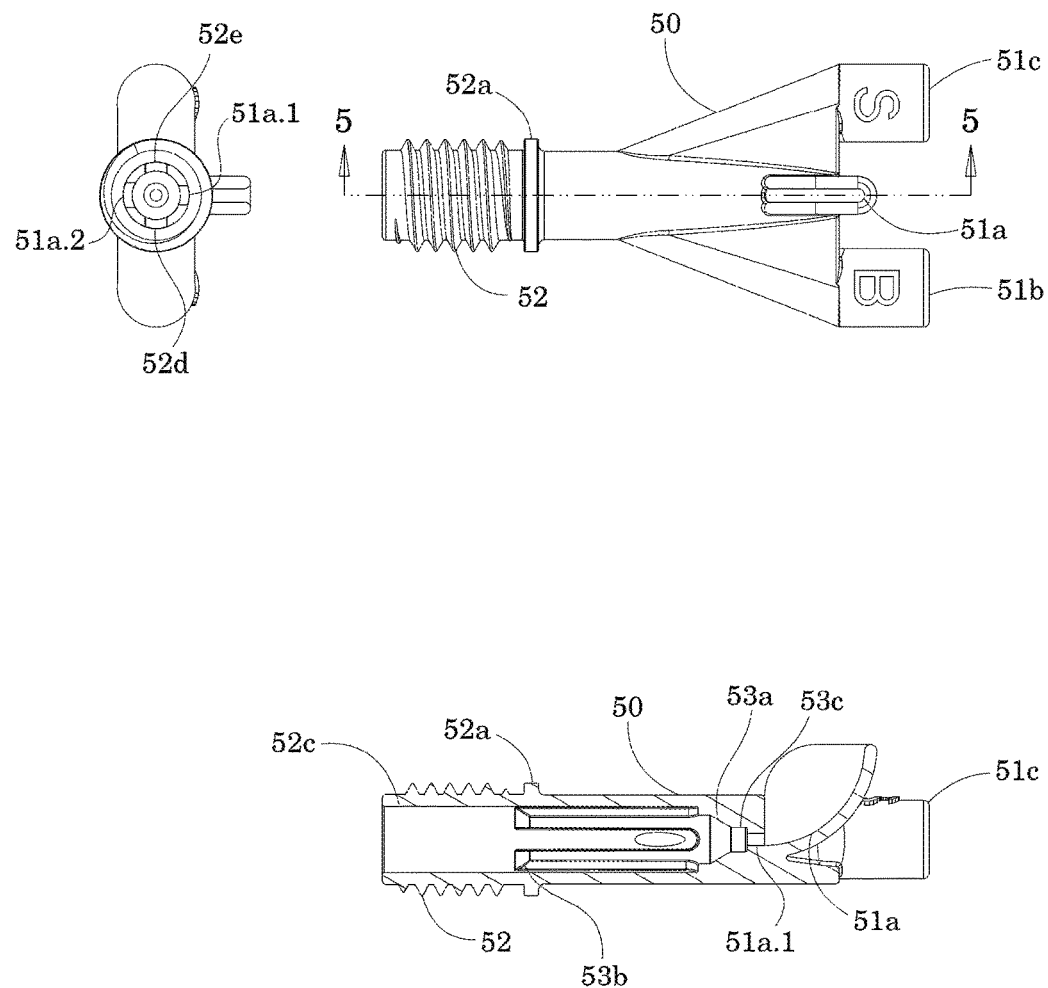
FIG. 11 is a top plan view, front plan view, and longitudinal side plan cross section view of the manifold, all in accordance with the invention.
Figure 12:
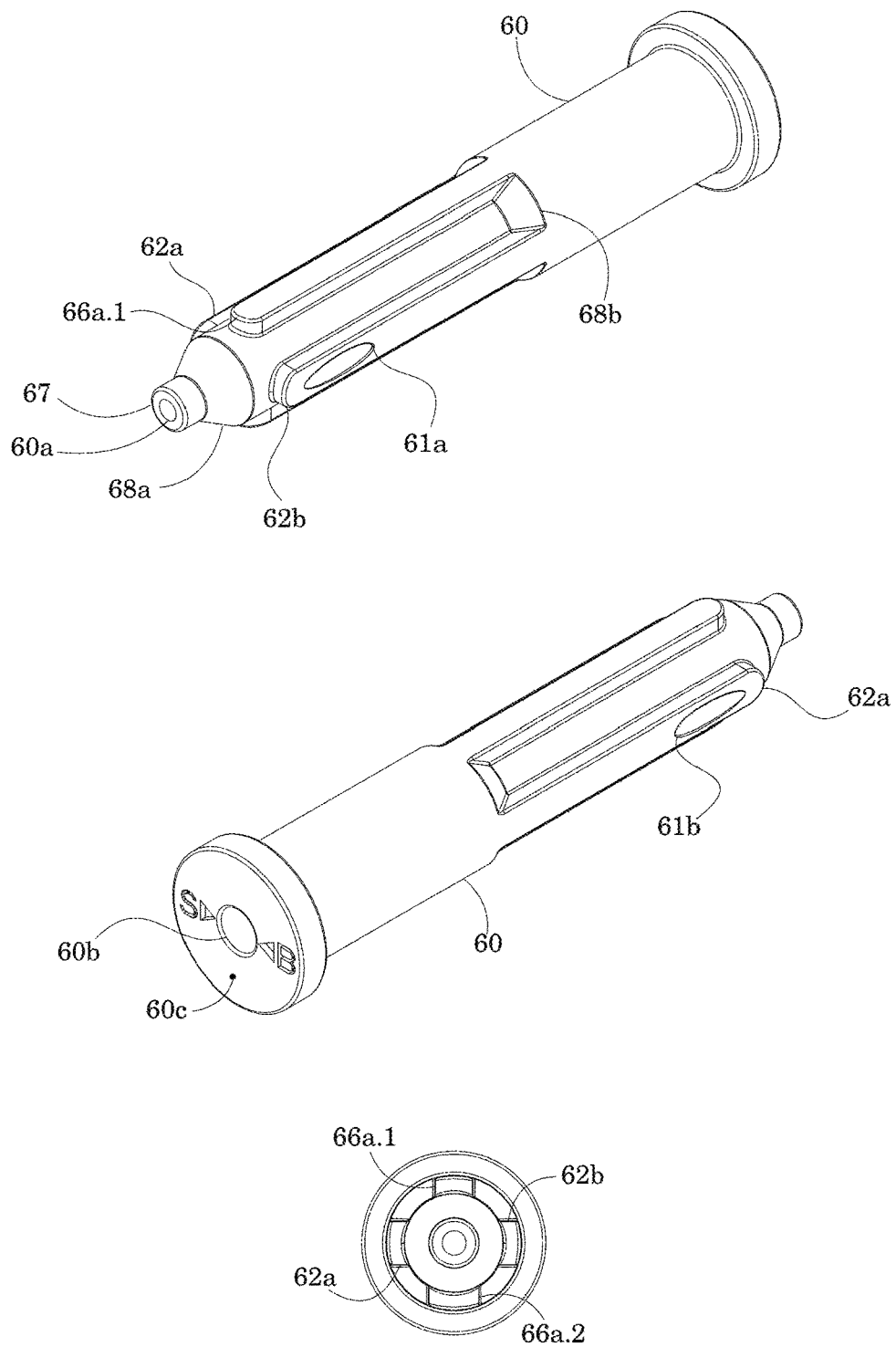
FIG. 12 is a distal and proximal isometric view and proximal plan view of the solution channel insert, all in accordance with the invention.
Figure 13:
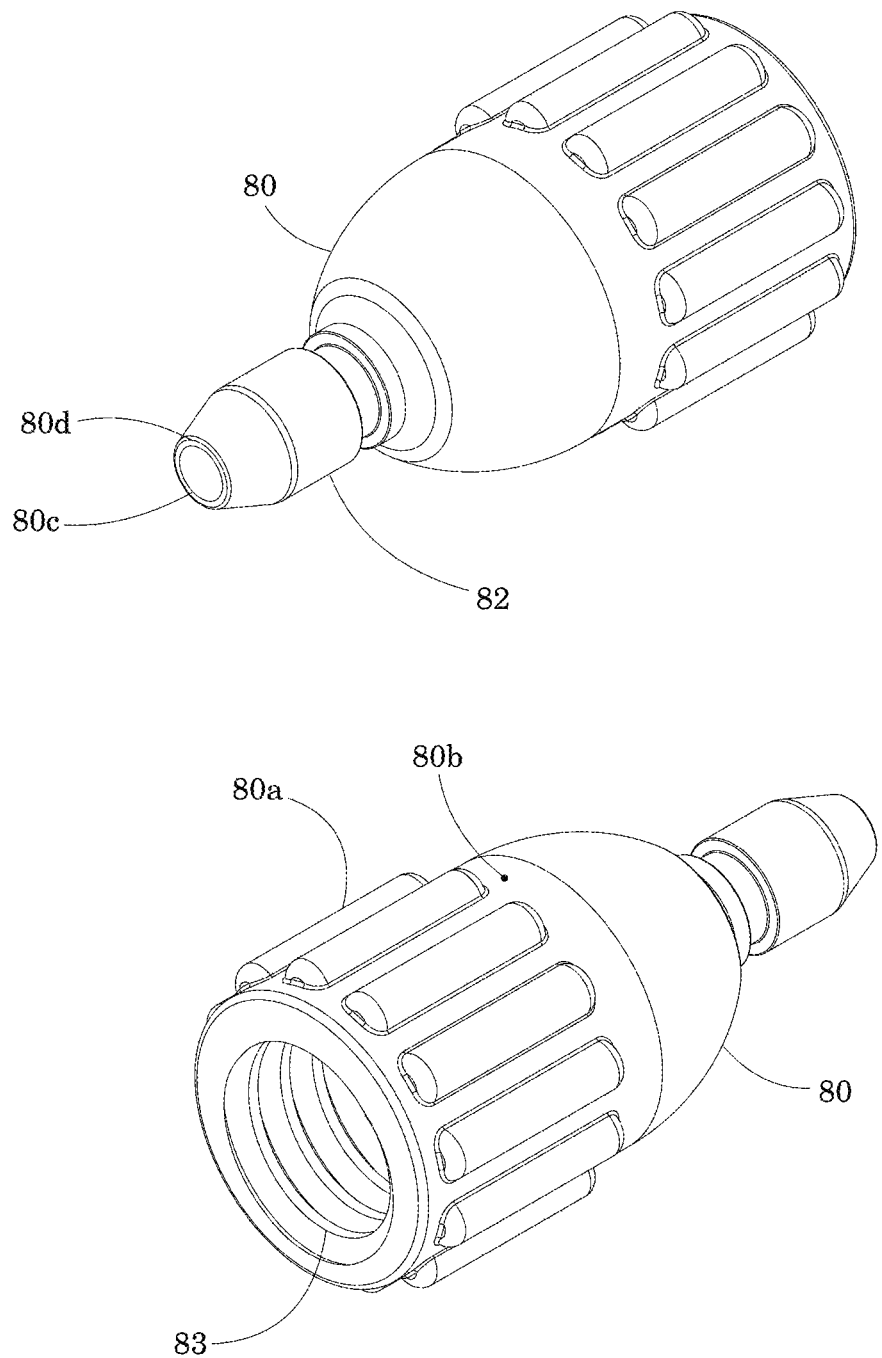
FIG. 13 is a distal and proximal isometric view of the retainer cap, all in accordance with the invention.

The manifold 50 includes a configuration FIG. 11 for the mating of the retainer cap 80. The male thread mating configuration 52 on the manifold located in the distal area which is also comprised of a proximal flange 52a joins with FIG. 13 the inner aperture female thread surface 83 of the retainer cap 80 on the outer surface 80b of the retainer cap a radial pattern of longitudinal protrusions 80a provide a gripping surface for the tightening of the cap 80 to the manifold 50, the distal area 82 is configured to accept the strain-relief 81, an aperture along the longitudinal centerline 80c extending from the most distal surface 80d terminating on surface 80e is sized to allow the passage of the multi-lumen 90. When joined the combined elements create a compression seal between the solution channel insert 60 and manifold 50, this is accomplished by the retainer cap surface 80e coming in contacting with and applying force upon the solution channel insert surface 60c resulting in a compression seal. The manifold 50 distal area has an aperture 52c which is proportioned to allow insertion and joining of the solution channel insert 60 with the manifold 50 a first rail channel 52d with an opposing second rail channel 52e located on the horizontal longitudinal center plane of manifold 50 that join with a first rail 62a and opposing second rail 62b located on the horizontal longitudinal center plane of the solution channel insert 60 FIG. 12. To insure proper alignment of the solution channel insert 60 with the manifold 50 a first rail channel 51a.1 with an opposing second rail channel 51a.2 located on the vertical longitudinal center plane of manifold 50 and proportioned to control the insertion position of the solution channel insert 60 join with a first rail 66a.1 and opposing second rail 66a.2 located on the vertical longitudinal center plane of the solution channel insert 60. Two angled surfaces 68a and 68b correspond to surfaces 53a and 53b of the manifold 50 to create a positive seal when the components are joined. A additional feature which aids in alignment during assembly of the solution channel insert 60 and manifold 50 is a proximal protrusion 67 which corresponds with a recess 53c of the manifold 50 which ensures proper positioning/alignment of the solution channel insert 60. An orifice 60b sized proportionately to accommodate insertion of the multi-lumen 90.

Figure 9:
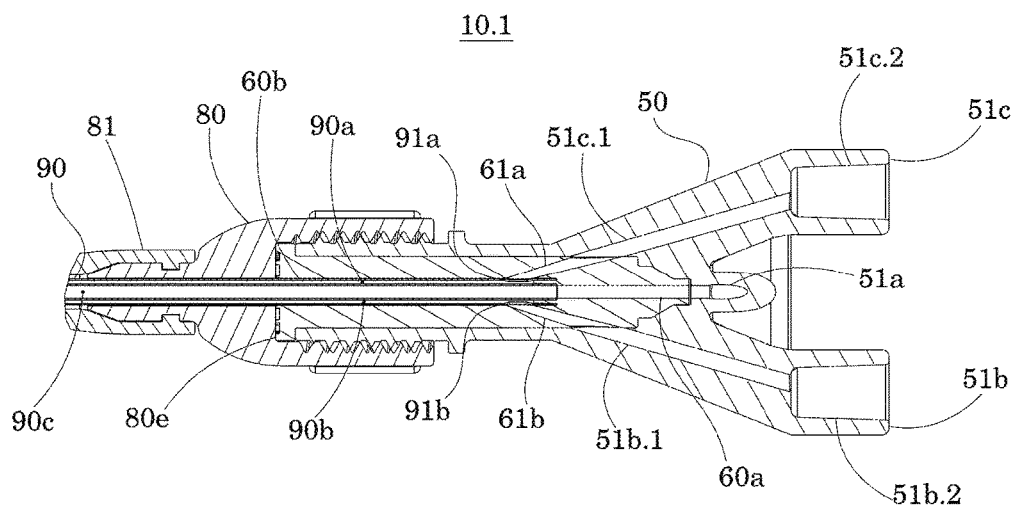
FIG. 9 is a partial side plan view and longitudinal top cross section plan view of the manifold, solution channel insert, multi-lumen, and retainer cap with strain-relief in final assembly as they would be configured in normal usage of the dual syringe delivery device, all in accordance with the invention.
Figure 9:
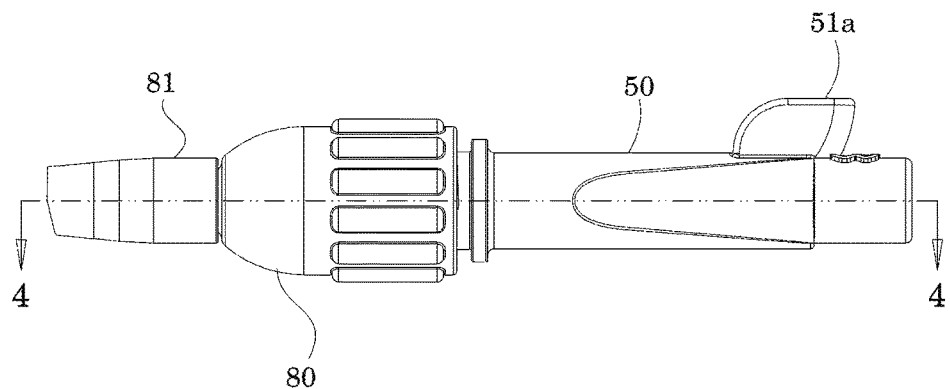
Figure 10:
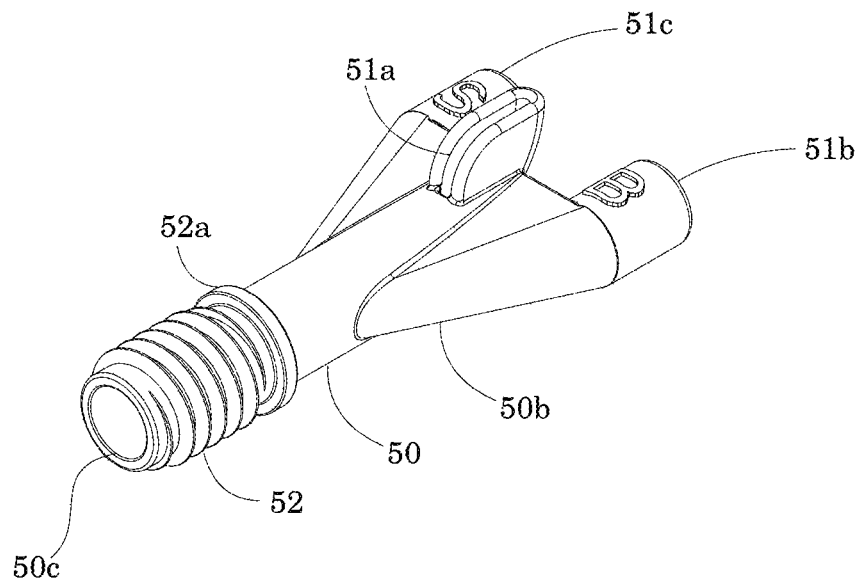
FIG. 10 is a distal and proximal isometric view of the manifold, all in accordance with the invention.
Figure 10:
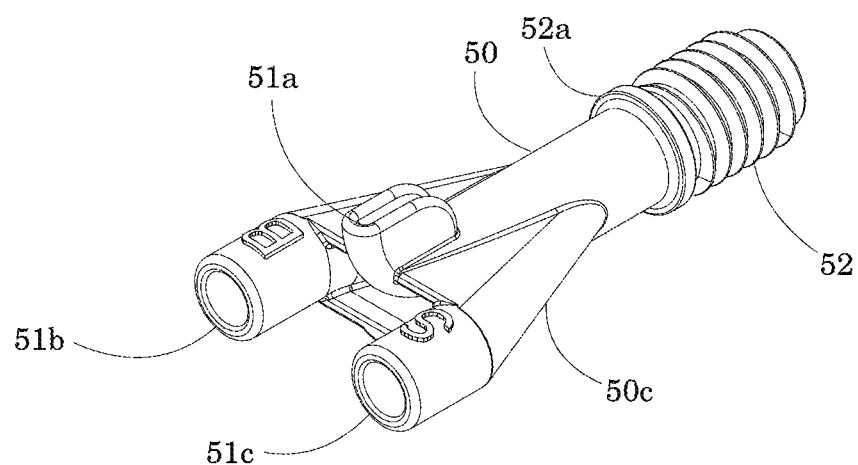

As shown in FIG. 9 cross section 4-4 of illustrates the manifold 50 joined with the retainer cap 80 joined to the strain relief 81 and solution channel insert 60 joined to multi-lumen 90. Further illustrated is the manifold 50 with its guidewire channel 51a and first 51b and second 51c unvalved solution channels with each channel having corresponding unvalved tapered channels 51b.1 and 51c.1 traversing into the corresponding unvalved channels 61a and 61b of the solution channel insert 60. The unvalved channels 61a and 61b of the solution channels insert 60 traverse into corresponding proximal orifices 91a and 91b of the multi-lumen 90. The manifold guidewire channel 51a join with corresponding solution channel insert 60 central guidewire channel 60a and the multi-lumen 90 central orifice 90c.

In application the two fluid solutions are introduced into the manifold 50 solution channels 51b.1 and 51c.1 via commonly actuable reservoirs then out though the corresponding solution channels 61a, and 61b in the solution channel insert 60 then through the solution channels 90a and 90b of the multi-lumen 90. The solutions entering at the most proximal end 90f which terminates at the solution channel insert 60 then traversing distally through the multi-lumen 90 solution channels 90a and 90b to the most distal end 90e of the multi-lumen 90 and terminating at the distal tip 71 forcing the solutions to be exhausted through corresponding orifices. The sclerosing solution traverse though solution channel 90a and exhaust through first orifices 92a.1, and second orifice 92a.2 into the plenum 70a of the outer balloon 70; the saline solution traverse though balloon/solution channel 90b and exhaust through first orifices 92b.1, and second orifice 92b.2 into the plenum 75a of the inner balloon 75. With the outer balloon 70 being perforated and the inner balloon 75 being void of any orifices as the solutions inner the respective balloons the expansion of the inner balloon 75 forces the solution entering the outer balloon 70 out through the perforation orifices 70b and into the vein wall.

Figure 14:
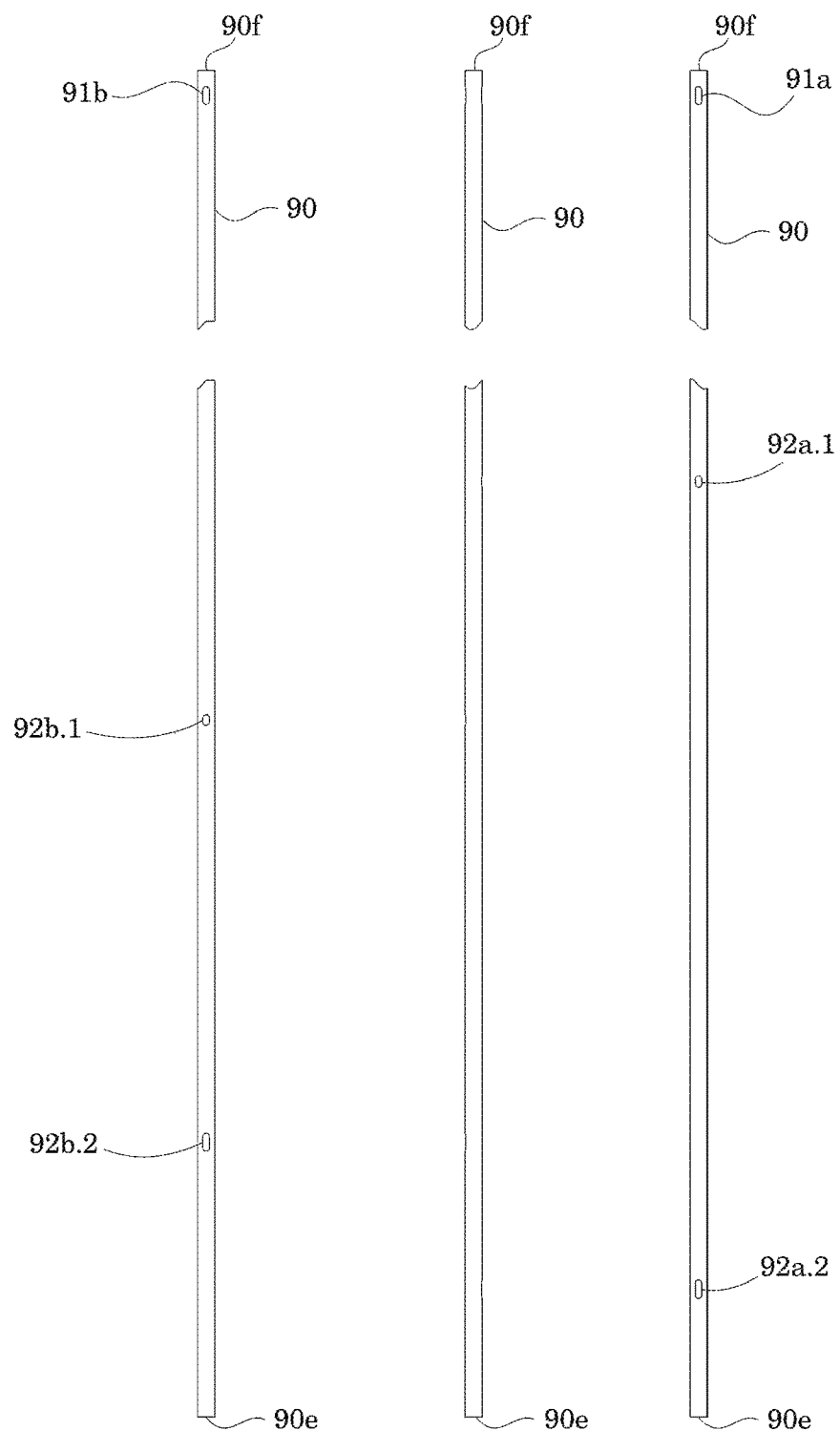
FIG. 14 is a top, right side, and left side plan views of the multi-lumen, all in accordance with the invention.
Figure 15:
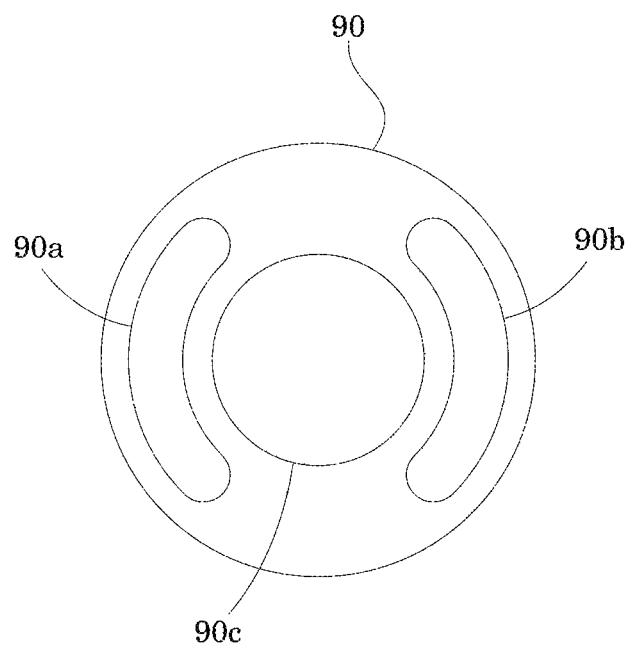
FIG. 15 is an increased scale front plan view of the multi-lumen, all in accordance with the invention.

As shown in FIGS. 14 and 15, illustrates the multi-lumen 90 with solution channels 90a and 90b and central orifice 90c which extends from the proximal end 90f to the distal end 90e. Located along the longitudinal centerline of the multi-lumen 90 are three orifices for the solution channel 90a, a first proximally positioned solution entry orifice 91a and a distally positioned first exhaust orifices 92a.1, and second exhaust orifice 92a.2. Located along the longitudinal centerline of the multi-lumen 90 are three orifices for the balloon/solution channel 90b, a first proximally positioned solution entry orifice 91b and a distally positioned first exhaust orifices 92b.1, and second exhaust orifice 92b.2.

Figure 16:
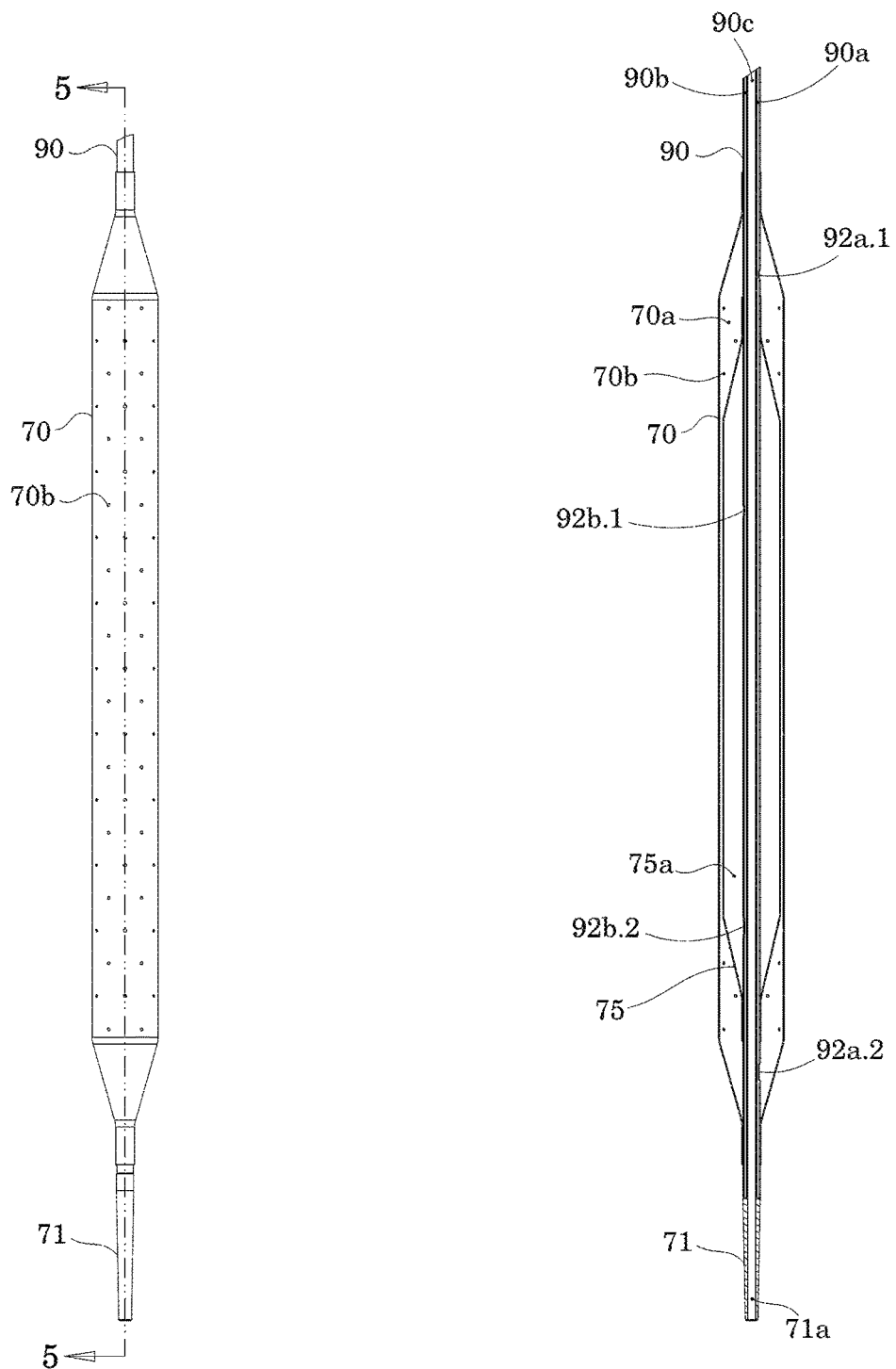
FIG. 16 is a partial top plan and longitudinal cross section view of the inner and outer dual balloon catheter assembly, all in accordance with the invention.

As shown in FIG. 16, illustrates the outer balloon 70 and inner balloon 75 as configured with and joined to the multi-lumen 90 positioned proximal of the distal lumen tip 71. Residing in the plenum 70a of the outer balloon 70 the inner balloon 75 with its plenum 75a and void of any orifices is further illustrated with the first orifice 92b.1, and second orifice 92b.2 opening into the plenum 75a of the inner balloon 75. The expansion of the inner balloon plenum 75a can be controlled by varying the size, plurality, and position of the orifices 92b.1 and 92b.2. The outer balloon 70 with its perforation orifices 70b being positioned over and overlapping on the distal and proximal ends of the inner balloon 75 and with the first orifice 92a.1, and second orifice 92a.2 opening into the plenum 70a of the outer balloon 70. The expansion of the outer balloon plenum 70a can be controlled by varying the size, plurality, and position of the orifices 92a.1 and 92a.2. The outer balloon 70 with perforated orifice pattern 70b allows for the sclerosing solution to be deployed, the rate, volume, and pattern of the solution disbursement can be controlled by varying the perforation orifice 70b size, and pattern.

Figure 17:
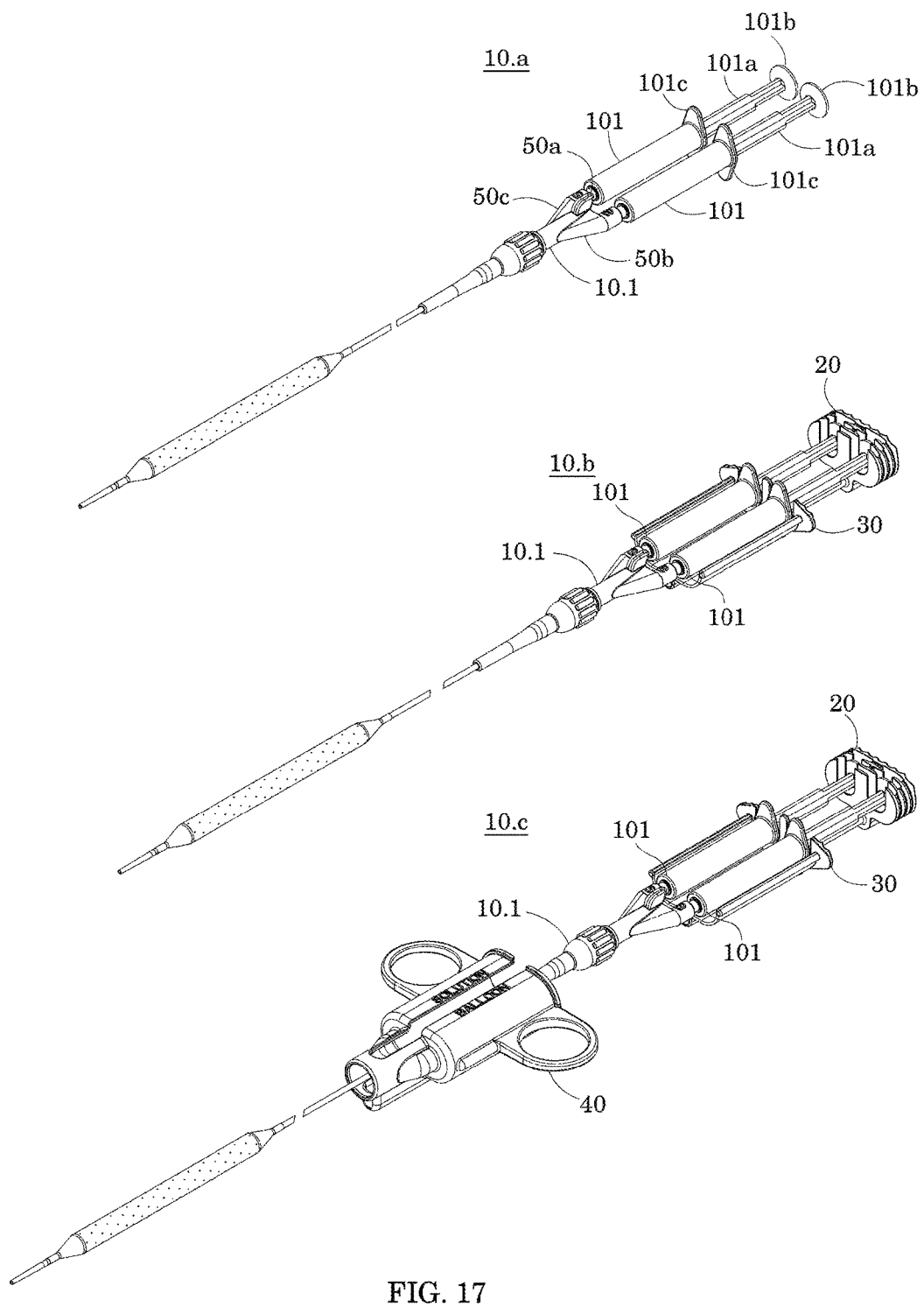
FIG. 17 is an isometric view of the normal progression/method of loading the dual syringes and dual balloon catheter assembly into the plunger and cradle components readied for insertion into the holster to complete the final assembly as they would be configured in normal usage of the dual balloon dual syringe delivery device, all in accordance with the invention.

As shown in FIG. 17, illustrates the method of use for the dual balloon dual syringe delivery device 10.a illustrates step one of inserting, the two pre-loaded 2 ml syringes 101 with the plungers 101a fully extended, into the manifold 50 of the dual balloon catheter assembly 10.1; 10.b illustrates step two of loading the two syringes 101 and dual balloon catheter assembly 10.1 into position in the, plunger 20 and cradle 30; 10.c illustrates step three "the final step" of loading the two syringes 101, dual balloon catheter assembly 10.1, cradle 30 and plunger 20 into the holster 40 and readied for use.

In practice, the invention provides a method of dispensing a sclerosing solution. The method collectively comprised of a plunger, cradle, holster, and dual balloon catheter assembly which accepts solution delivery systems e.g. syringes.

The foregoing description is considered as illustrative only of the principles of the invention. Further, since numerous modifications and changes may readily occur to those skilled in the art, it is not desired to limit the invention to the exact construction and operation shown and described, and accordingly, all suitable modifications and equivalents are considered to fall within the scope of the invention. Various features and advantages of the invention are set forth in the following claims.

All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

The invention claimed is:

1. A dual balloon dual syringe delivery device with commonly actuable reservoirs for each solution component, comprising:
   a manifold;
   a multi-lumen tube having a distal tip;
   an inner balloon;
   an outer balloon;
   a plunger;
   a cradle;
   a holster;
   the manifold comprising: a first solution channel and a second solution channel;
   a solution channel insert;
   a retainer cap;
   wherein the first solution channel and the second solution channel are non-converging;
   wherein the solution channel insert is in direct mating relationship with a distal portion of the manifold;
   wherein the retainer cap is in direct mating relationship with the distal portion of the manifold;
   wherein the solution channel insert is in direct mating relationship with the proximal portion of the multi-lumen tube and having apertures through which fluids are dispensed into the multi-lumen tube;

wherein the multi-lumen tube is in direct mating relationship with the inner and outer balloons;

wherein the multi-lumen tube having a first solution lumen in fluid connection with said first solution channel, a second solution lumen in fluid connection with said second solution channel, and a central longitudinal lumen;

wherein the multi-lumen tube having at the proximal end a first solution inlet in fluid connection with said first solution lumen, and a second solution inlet in fluid connection with said second solution lumen;

wherein the first solution lumen further comprises a first plurality of exhaust orifices configured to be fluidly connected to the inner balloon, and the second solution lumen further comprises a second plurality of exhaust orifices configured to be fluidly connected to the outer balloon;

wherein the inner balloon having an inner surface and an outer surface void of any orifices;

wherein the outer balloon having an inner surface and an outer surface arrayed with multiples of orifices;

wherein the plunger having a proximal head and a distally extending shaft that joins with an aperture in the cradle;

wherein the cradle having a proximal flange and a distally extending body which joins with an aperture of the holster;

wherein the holster having a proximal flange, a distally extending body, and an interior aperture.

2. The manifold of claim 1, further comprising a plurality of recessed groove elements sized to receive corresponding protrusions on the solution channel insert which insures proper alignment.

3. The manifold of claim 1, wherein the retainer cap comprises a central longitudinal orifice.

4. The manifold of claim 1, wherein the solution channel insert comprises a first channel in fluid connection with the first solution channel, and a second channel in fluid connection with the second solution channel.

5. The manifold of claim 1, wherein female locking luer is provided at the proximal end of each of the first solution channel and the second solution channel.

6. The manifold of claim 1, wherein female slip luer is provided at the proximal end of each of the first solution channel and the second solution channel.

7. The plunger of claim 1, wherein the plunger proximal head is configured to receive a hypodermic syringe plunger head.

8. The plunger of claim 1, wherein the plunger proximal head provides for actuating the fluid solution reservoirs.

9. The plunger of claim 1, wherein the shaft is in direct mating relationship with the cradle.

10. The cradle of claim 1, wherein the body is in direct mating relationship with the holster.

11. The cradle of claim 1, wherein the body is in direct mating relationship with a syringe finger tab.

12. The holster of claim 1, wherein the body is in direct mating relationship with the manifold.

13. The multi-lumen tube of claim 1, wherein the sizing and number of distal apertures control a rate of solution flow, and a rate of balloon expansion.

14. The multi-lumen tube of claim 1, wherein the distal tip is a separate component in direct mating relationship with the multi-lumen tube.

\* \* \* \* \*